(12) United States Patent
Okada et al.

(10) Patent No.: US 6,566,392 B1
(45) Date of Patent: May 20, 2003

(54) SOLID FORMULATION

(75) Inventors: Kenya Okada, Takarazuka (JP); Satoshi Sembo, Nishinomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/241,528

(22) Filed: Sep. 12, 2002

(30) Foreign Application Priority Data

Sep. 14, 2001 (JP) .......................................... 2001-279521

(51) Int. Cl.⁷ .......................... A01N 43/08; A61K 31/34
(52) U.S. Cl. ........................................ 514/461; 514/471
(58) Field of Search .................................. 514/461, 471

(56) References Cited

FOREIGN PATENT DOCUMENTS

| EP | 0110564 A | 6/1984 |
|---|---|---|
| EP | 0127773 A | 12/1984 |
| JP | 6-336404 | 6/1994 |
| JP | 10-139604 | 5/1998 |
| JP | 2000-53505 A | 2/2000 |

*Primary Examiner*—Alton N Pryor
(74) *Attorney, Agent, or Firm*—Birch, Stewart, Kolasch & Birch, LLP

(57) ABSTRACT

The present invention provides a solid formulation comprising (a) 10–40% by weight of 1-methyl-2-nitro-3-[(3-tetrahydrofuryl)methyl]guanidine, (b) 5–30% by weight of at least one carbonate selected from sodium hydrogencarbonate, sodium carbonate and potassium carbonate, (c) 5–30% by weight of at least one solid acid selected from citric acid and malic acid and (d) 10–80% by weight of a feed and/or attractant for flies, that is light and easy-handling in view of possibility of quickly dissolving it at the application place.

5 Claims, No Drawings

SOLID FORMULATION

FIELD OF THE INVENTION

The present invention relates to a new formulation of 1-methyl-2-nitro-3-[(3-tetrahydrofuryl)methyl]guanidine, which is a solid formulation for preparing aqueous bait for controlling flies.

BACKGROUND ART

1-Methyl-2-nitro-3-[(3-tetrahydrofuryl)methyl]guanidine is an excellent insecticidal compound described in, for example, U.S. Pat. No. 5,532,365. Further, it is provided to try this compound to use as an active ingredient for baits in JP-Hei-10-139604A. However, the controlling effects for pests are unsatisfactory when said compound is utilized for usual solid baits. Furthermore, aqueous baits containing said compound as an insecticidal ingredient are suggested in JP-2000-53505A. However, the weight of the aqueous bait composition is large as the content of water in the composition is large. Therefore, the composition is bulky and heavy, and the increase of the distributive cost for transportation or storage is worried.

The object of the present invention is to provide a portable solid formulation for preparing an aqueous baits containing 1-methyl-2-nitro-3-[(3-tetrahydrofuryl)methyl]guanidine (hereinafter, referred to as dinotefuran) as an insecticidal ingredient.

SUMMARY OF THE INVENTION

The present invention provides a solid formulation which comprises (a) 10–40% by weight of dinotefuran, (b) 5–30% by weight of at least one carbonate selected from sodium hydrogencarbonate, sodium carbonate and potassium carbonate, (c) 5–30% by weight of at least one solid acid selected from citric acid and malic acid and (d) 10–80% by weight of a feed and/or attractant for flies. Further, it provides an aqueous formulation that is obtainable by dissolving or dispersing the solid formulation described above with water. Furthermore, it also provides a method for controlling flies that comprises applying the aqueous formulation to a place where flies inhabit.

DETAILED DESCRIPTION OF THE INVENTION

Dinotefuran is a known insecticidal compound, and it is utilized for agricultural use. It can be obtained according to the description of U.S. Pat. No. 5,532,365 or provided by Mitsui Chemical.

The solid formulation of the present invention contains 10–40% by weight of dinotefuran.

The carbonate utilized in the present invention is sodium hydrogencarbonate, sodium carbonate or potassium carbonate, and the carbonate may be one carbonate solely or a mixture of two or more at any mixing ratio. The content of the carbonate is 5–30% by weight in the present solid formulation.

The solid acid utilized in the present invention is citric acid or malic acid, and the solid acid may be one solid acid solely or a mixture of two at any mixing ratio. The content of the solid acid is 5–30% by weight in the present solid formulation.

In the solid formulation of the present invention, the weight ratio of dinotefuran and the carbonate is usually 4:1 to 1:3, preferably 2:1 to 1:2. Further, the weight ratio of the carbonate and the solid acid is usually 2:1 to 1:2 in the solid formulation of the present invention.

The solid formulation of the present invention contains 10–80% by weight of a feed and/or attractant for flies. Examples of the feed and attractant for flies include saccharides such as sucrose, glucose, fructose, lactose, dextrin and starch that is originated from corn, potato, sweat potato and so on; crop powder such as flour, rice powder, corn powder, potato powder; fish powder, animal powder and insect powder such as beef, shrimps, crabs, fish and insects; dairy products such as skim milk and dried cheese powder; attractants such as 9-tricosene; acetal (acetaldehyde diethyl acetal) and trimethylamine acid adducts (e.g. trimethylamine hydrochloride, trimethylamine hydrobromide). The content of the feed and/or attractant for flies is 10–80% by weight, preferably 30–70% by weight in the present solid formulation.

The solid formulation of the present invention may also contain a desiccant for preventing chemical reaction in preservation such as anhydrous sodium sulfate, calcium oxide and magnesium oxide. Further, it may optionally contain a coloring agent such as tar dyes and a fungicide such as benzoate esters and sorbic acid.

The powdery solid formulation of the present invention can be obtained by mixing and pulverizing dinotefuran, the above-mentioned carbonate, the above-mentioned solid acid and the feed and/or attractant, optionally the desiccant, coloring agent, fungicide and so on. The tablets or granules of the solid formulation of the present invention can be obtained by further granulation with tablet machine or bricketting machine.

The solid formulation of the present invention is usually added to water at the ratio of 0.0025 g to 500 g per 1 liter, and it is easily dissolved to produce aqueous bait, which is the aqueous formulation of the present invention.

The obtained aqueous formulation can be applied to a place where flies inhabit for controlling the flies. Typical application methods of the aqueous formulation include a method for applying it by power sprayer to a place where flies inhabit; a method for coating a place where flies inhabit such as floor, wall, pillar and so on by using brush, roller and so on; and a method for applying it by setting non-woven cloth, sponge, cotton absorbing it to a place where flies inhabit.

When the aqueous formulation is applied to a place where flies inhabit, the application rate is usually 0.01 mg to 1000 mg, preferably 0.1 mg to 250 mg of dinotefuran per 1 $m^2$ of the floor area of the place for controlling flies.

The place where flies inhabit is typically floor, wall, ceiling and pillar in houses, cattle sheds and so on; food, feed and cattle's neighborhood; and so on. Examples of the flies include *Musca domestica* (housefly), *Muscina stabulans* (false housefly), *Fannia canicularis* (little housefly), Phoridae, Drosophilidae (vinegar flies) and Psychodidae (moth flies).

EXAMPLES

The present invention will be explained in detail below.

Formulation Example 1

Five grams (5 g) of dinotefuran, 2 g of sodium hydrogencarbonate, 2 g of malic acid and 5 g of sucrose (white powder sugar produced by Taito Co., Ltd.) were mixed and pressed under 2 tons for one minute by tablet machine (Shimadzu SSP-10A) to give 14 g of round Formulation 1 having 30 mm in diameter.

Formulation Example 2

Formulation 2 was obtained by the same procedure as Formulation example 1 except that citric acid was used in place of malic acid.

Formulation Example 3

Formulation 3 was obtained by the same procedure as Formulation example 2 except that sodium carbonate was used in place of sodium hydrogencarbonate.

Formulation Example 4

Formulation 4 was obtained by the same procedure as Formulation example 2 except that potassium carbonate was used in place of sodium hydrogencarbonate.

Formulation Example 5

A half gram (0.5 g) of dinotefuran, 0.5 g of sodium hydrogencarbonate, 0.5 g of citric acid and 1.0 g of sucrose (white powder sugar produced by Taito Co., Ltd.) were mixed and pressed under 2 tons for one minute by tablet machine (Shimadzu SSP-10A) to give 2.5 g of round Formulation 5 having 30 mm in diameter.

Formulation Example 6

Sixteen and a half grams (16.5 g) of dinotefuran, 5 g of sodium hydrogencarbonate, 5 g of citric acid, 23.4 g of sucrose (white powder sugar produced by Taito Co., Ltd.) and 0.1 g of a coloring agent (Blue No. 1 listed in the appendix tables of the ministerial ordinance of the Ministry of Health, Labour and Welfare) are mixed and pressed under 2 tons for one minute by tablet machine (Shimadzu SSP-10A) to give 50 g of round Formulation 6 having 30 mm in diameter.

Reference Example 1

Reference Formulation 1 was obtained by the same procedure as Formulation example 1 except that succinic acid was used in place of malic acid.

Reference Example 2

Reference Formulation 2 was obtained by the same procedure as Formulation example 2 except that magnesium carbonate was used in place of sodium hydrogencarbonate.

Reference Example 3

Five grams (5 g) of dinotefuran and 5 g of sucrose (white powder sugar produced by Taito Co., Ltd.) were mixed in a mortar uniformly to give Reference Formulation 3.

Reference Example 4

A half gram (0.5 g) of dinotefuran, 0.5 g of sodium hydrogencarbonate, 0.5 g of maleic acid and 1.0 g of sucrose (white powder sugar produced by Taito Co., Ltd.) were mixed and pressed under 2 tons for one minute by tablet machine (Shimadzu SSP-10A) to give 2.5 g of round Reference Formulation 4 having 30 mm in diameter.

Test example 1

Each of Formulations 1–4 obtained in Formulation Examples 1–4 was added into 100 mL of distilled water, and observed the solubility after 5 minutes. Further, each of Reference Formulations 1–3 obtained in Reference Examples 1–3 was added into 100 mL of distilled water, and observed the solubility after 5 minutes. The results are given in Table 1.

TABLE 1

| Tested Formulation | Insecticidal Ingredient | Carbonate | Solid Acid | Feed | Observed Result |
|---|---|---|---|---|---|
| Formulation 1 | Dinotefuran | Sodium hydrogen carbonate | Malic Acid | Sucrose | ○ |
| Formulation 2 | Dinotefuran | Sodium hydrogen carbonate | Citric Acid | Sucrose | ○ |
| Formulation 3 | Dinotefuran | Sodium carbonate | Citric Acid | Sucrose | ○ |
| Formulation 4 | Dinotefuran | Potassium carbonate | Citric Acid | Sucrose | ○ |
| Reference Formulation 1 | Dinotefuran | Sodium hydrogen carbonate | Succinic Acid | Sucrose | X |
| Reference Formulation 2 | Dinotefuran | Magnesium carbonate | Citric Acid | Sucrose | X |
| Reference Formulation 3 | Dinotefuran | — | — | Sucrose | X |

○: Completely dissolved
X: Partially not dissolved, Observed precipitation

Test example 2

Formulation 5 obtained in Formulation Example 5 was dissolved in distilled water to make the total 100 mL. One milliliter (1 mL) of the obtained aqueous solution was dropped on a board (15 cm×15 cm) with a pipette.

In a glass chamber (70 cm×70 cm×70 cm), 20 adult houseflies (10 males and 10 females) were released and set the above-treated board on the floor of the glass chamber. After 2 hours, the number of the knocked-down houseflies was investigated, and soon all the houseflies were collected, moved to a clean vessel and gave baits (skim milk) and water. The mortality was observed after 24 hours. The tests were carried out by three repetitions.

Further, the same test was carried out for Reference Formulation 4 obtained in Reference Example 4.

The results are given in Table 2.

TABLE 2

| | Dosage of Compound A (mg/m$^2$) | Knock-down ratio after 2 hours (%) | Mortality after 24 hours (5) |
|---|---|---|---|
| Formulation 5 | 10 | 83 | 100 |
| Reference Formulation 4 | 10 | 3 | 10 |

The present invention provides a solid formulation for preparing aqueous bait formulation for flies which is light and easy-handling in view of possibility of quickly dissolving it at the application place. Further, the aqueous bait formulation is very effective for controlling flies.

We claim:

1. A solid formulation which comprises (a) 10–40% by weight of 1-methyl-2-nitro-3-[(3-tetrahydrofuryl)methyl]guanidine, (b) 5–30% by weight of at least one carbonate selected from sodium hydrogencarbonate, sodium carbonate and potassium carbonate, (c) 5–30% by weight of at least one solid acid selected from citric acid and malic acid and (d) 10–80% by weight of a feed and/or attractant for flies.

2. A solid formulation according to claim 1, wherein the feed and/or attractant for flies is a saccharide.

3. A solid formulation according to claim 1, wherein the feed and/or attractant for flies is sucrose.

4. An aqueous formulation that is obtainable by dissolving or dispersing the solid formulation described in claim 1 with water.

5. A method for controlling flies which comprises applying the aqueous formulation described in claim 4 to a place where flies inhabit.

* * * * *